US008115003B2

(12) United States Patent
Salbeck et al.

(10) Patent No.: US 8,115,003 B2
(45) Date of Patent: Feb. 14, 2012

(54) PYRIDO[3,2-H]QUINAZOLINES AND/OR 5,6-DIHYDRO DERIVATIVES THEREOF, A METHOD FOR THE PRODUCTION THEREOF AND DOPED ORGANIC SEMICONDUCTOR MATERIAL CONTAINING THESE

(75) Inventors: Josef Salbeck, Kaufengen (DE); Manfred Kussler, Abbruck (DE); Andrea Lux, Dresden (DE)

(73) Assignee: Novaled AG, Dresden (DE)

( * ) Notice: Subject to any disclaimer, the term of this patent is extended or adjusted under 35 U.S.C. 154(b) by 0 days.

(21) Appl. No.: 12/868,465

(22) Filed: Aug. 25, 2010

(65) Prior Publication Data

US 2011/0046374 A1 Feb. 24, 2011

Related U.S. Application Data

(62) Division of application No. 12/046,620, filed on Mar. 12, 2008, now Pat. No. 7,807,687.

(30) Foreign Application Priority Data

Mar. 16, 2007 (DE) .......................... 10 2007 012794

(51) Int. Cl.
*C07D 215/12* (2006.01)
*C07D 215/14* (2006.01)

(52) U.S. Cl. ...................................................... 546/168

(58) Field of Classification Search ................... 546/168
See application file for complete search history.

(56) References Cited

U.S. PATENT DOCUMENTS

| | | | | |
|---|---|---|---|---|
| 5,093,698 | A | 3/1992 | Egusa | |
| 5,811,833 | A | 9/1998 | Thompson | |
| 6,013,384 | A | 1/2000 | Kido et al. | |
| 7,186,841 | B2 * | 3/2007 | Browner et al. | 546/168 |
| 2009/0212280 | A1 | 8/2009 | Werner et al. | |

FOREIGN PATENT DOCUMENTS

WO WO03/088271 A1 10/2003

OTHER PUBLICATIONS

Anderson, J.D. et al. "Electrochemistry and Electrogenerated Chemiluminescence Processes of the Components of Aluminum Quinolate/Triarylamine, and Related Organic Light-emitting Diodes," J. Am. Chem. Soc. 120, 1998, 9646.

Andrade, B.W. et al. "Relationship between the ionization and oxidation potentials of molecular organic semiconductors," Org. Electron. 6, 2005, 11.

Bard, A.J. & Faulkner, L.R."Electrochemical Methods: Fundamentals and Applications," Wiley, 2nd Edition, 2000 (Chapter 2 excerpt).

Bard, A.J. & Faulkner, L.R."Electrochemical Methods: Fundamentals and Applications," Wiley, 2nd Edition, 2000 (Chapter 6 excerpt).

Fu, Y. et al. "Quantum-chemical Predictions of Absolute Standard Redox Potentials of Diverse Organic Molecules and Free Radicals in Acetonitrile," J. Am. Chem. Soc. 127, 2005, 7227-7234.

Gao, W. et al. "Effect of electrical doping on molecular level alignment at organic-organic heterojunctions," Appl. Phys. Lett. 82, 2003, 4815.

Harada, K. et al. "Organic Homojunction Diodes with a High Built-In Potential: Interpretation of the Current-Voltage Characteristics by a Generalized Einstein Relation," Phys. Rev. Lett. 94, 2005, 036601.

Huang, J.S. et al. "Low-voltage organic electroluminescent devices using pin structures," Appl. Phys. Lett. 80, 2002, 139.

Kido, J. et al. "Bright organic electroluminescent devices having a metal-doped electron-injecting layer," Appl. Phys. Lett. 73, 1998, 2866.

Maitrot, M. et al. "Molecular material based junctions: Formation of a Schottky contact with metallophthalocyanine thin films doped by the cosublimation method," J. Appl. Phys. 60(7), 1986, 2396-2400.

Miller, L.L. et al. "A Simple, Comprehensive Correlation of Organic Oxidation and Ionization Potentials," J. Org. Chem. 37, 1972, 916.

Nollau, A. et al. "Controlled n-type doping of a molecular organic semiconductor: Naphthalenetetracarboxylic dianhydride (NTCDA) doped with bis(ethylenedithio)-tetrathiafulvalane (BEDT-TTF)," J. Appl. Phys. 87 (9), 2000, 4340.

Parker, V.D. "On the Problem of Assigning Values to Energy Changes of Electrode Reactions," J. Am. Chem. Soc. 96, 1974, 5656.

Pfeiffer, M. et al. "Controlled doping of phthalocyanine layers by cosublimation with acceptor molecules: A systematic Seebeck and conductivity study," Appl. Phys. Lett. 73 (22), 1998, 3202.

Schlaf, R. et al. "HOMO/LUMO alignment at PCTDA/ZnPc and PTCDA/ClInPc Heterointerfaces Determined by Combined UPS and XPS Measurements," J. Phys. Chem. B. 103, 1999, 2984.

Tang, C.W. et al. "Organic electroluminescent diodes," Appl. Phys. Lett. 51 (12), 1987, 913.

Tang, T.B. "Ionization thresholds of merocyanine dyes in the solid state," J. Appl. Phys. 59, 1986, 5.

Werner, A.G. et al. "Pyronin B as a donor for n-type doping of organic thin films," Appl. Phys. Lett. 82, 2003, 4495.

Zhou, X. et al. "Very-low-operating-voltage organic light-emitting diodes using a p-doped amorphous hole injection layer," Appl. Phys. Lett., 78 (4), 2001, 410.

Zimmermann, T. et al. "Benzocycloalkenone und Dihydro-2H,7H-1-benzopyranone aus 2,4,6-triaryl-pyryliumsalzen und Cycloalkan-1,2-dionen," J. prakt. Chem. 331, 1989, 306-318. (English abstract only).

* cited by examiner

*Primary Examiner* — Andrew D Kosar
*Assistant Examiner* — Erich A Leeser
(74) *Attorney, Agent, or Firm* — Sutherland Asbill & Brennan LLP

(57) ABSTRACT

The present invention relates to pyrido[3,2-h]quinazolines and/or 5,6-dihydro derivatives thereof, methods for their production and doped organic semiconductor material which use such quinazolines.

2 Claims, No Drawings

PYRIDO[3,2-H]QUINAZOLINES AND/OR 5,6-DIHYDRO DERIVATIVES THEREOF, A METHOD FOR THE PRODUCTION THEREOF AND DOPED ORGANIC SEMICONDUCTOR MATERIAL CONTAINING THESE

This application is a divisional of U.S. application Ser. No. 12/046,620, filed Mar. 12, 2008, which claims priority to German Application No. 2007 10012794, filed Mar. 16, 2007. U.S. application Ser. No. 12/046,620 and German Application No. 2007 10012794 are incorporated by reference herein in their entirety.

The present invention relates to pyrido[3,2-h]quinazolines and/or 5,6-dihydro derivatives thereof, methods for their production and doped organic semiconductor material in which these quinazolines are employed.

BACKGROUND OF THE INVENTION

Since presenting organic light-emitting diodes and solar cells in 1989 [C. W. Tang et al., Appl. Phys. Lett. 51 (12), 913, (1987)], components made of organic thin films have been the subject of intensive research. Such films possess advantageous properties for the mentioned applications, such as e.g. efficient electroluminescence for organic light-emitting diodes, high absorption coefficients in the visible light range for organic solar cells, inexpensive production of the materials and manufacture of the components for simplest electronic circuits, amongst others. The use of organic light-emitting diodes for display applications already has commercial significance.

The performance characteristics of (optoelectronic) electronic multilayered components were determined from the ability of the layers to transport the charge carriers, amongst others. In the case of light-emitting diodes, the ohmic losses in the charge transport layers during operation are associated with the conductivity which, on the one hand, directly influences the operating voltage required, but, on the other hand, also determines the thermal load of the component. Furthermore, depending on the charge carrier concentration in the organic layers, bending of the band in the vicinity of a metal contact results which simplifies the injection of charge carriers and can therefore reduce the contact resistance. Similar deliberations in terms of organic solar cells also lead to the conclusion that their efficiency is also determined by the transport properties for charge carriers.

By doping hole transport layers with a suitable acceptor material (p-doping) or electron transport layers with a donor material (n-doping), respectively, the density of charge carriers in organic solids (and therefore the conductivity) can be increased substantially. Additionally, analogous to the experience with inorganic semiconductors, applications can be anticipated which are precisely based on the use of p- and n-doped layers in a component and otherwise would be not conceivable. The use of doped charge-carrier transport layers (p-doping of the hole transport layer by admixture of acceptor-like molecules, n-doping of the electron transport layer by admixture of donor-like molecules) in organic light-emitting diodes is described in U.S. Pat. No. 5,093,698.

Hitherto, the following approaches are known for improving the conductivity of organic vapour-deposited layers:

Increasing the charge carrier mobility by using electron transport layers consisting of organic radicals (U.S. Pat. No. 5,811,833), generating highly ordered layers which allow for an optimal overlap of the π orbital of the molecules, increasing the density of the mobile charge carriers by cleaning and careful treatment of the materials to avoid formation of charge-carrier adherence sites, doping organic layers with inorganic materials (alkaline metals: J. Kido et al., U.S. Pat. No. 6,013,384; J. Kido et al., Appl. Phys. Lett. 73, 2866 (1998), oxidants such as iodine, $SbCl_5$ etc.)

organic materials (TNCQ: M. Maitrot et al., J. Appl. Phys., 60 (7), 2396-2400 (1986), F4TCNQ: M. Pfeiffer et al., Appl. Phys. Lett., 73 (22) 3202 (1998), BEDT-TTF: A. Nollau et al., J. Appl. Phys., 87 (9), 4340 (2000), naphthalenedicarboxylic amides: M. Thomson et al., WO03088271, cationic dyes: A. G. Werner, Appl. Phys. Lett. 82, 4495 (2003))

organometallic compounds (metallocenes: M. Thomson et al., WO03088271)

metal complexes ($Ru^0$ $(terpy)_3$: K. Harada et al., Phys. Rev. Lett. 94, 036601 (2005).

While sufficiently strong, organic dopants already exist for p-doping (F4TCNQ), only inorganic materials, e.g. cesium, are available for n-doping. Through usage thereof, it has already been possible to achieve the improvement of the performance parameters of OLEDs. Thus, a dramatic reduction of the operating voltage of the light-emitting diode is reached by doping the hole transport layer with the acceptor material F4TCNQ (X. Zhou et al., Appl. Phys. Lett., 78 (4), 410 (2001)). It is possible to achieve a similar success by doping the electron-transporting layer with Cs or Li (J. Kido et al., Appl. Phys. Lett., 73 (20), 2866 (1998); J.-S. Huang et al., Appl. Phys. Lett., 80, 139 (2002)).

For a long time, a major problem in n-doping was that only inorganic materials were available for this process. However, using inorganic materials has the drawback that the atoms or molecules used can easily diffuse in the component due to their small size and thus can impede a defined production of sharp transitions from p-doped to n-doped areas, for example.

In contrast, the diffusion should play an inferior role when using large, space-filling, organic molecules as dopants as circuit crossing processes are only possible when higher energy barriers are overcome.

From WO 2005/086251 A2, the use of a metal complex as n-dopant for doping an organic semiconductor matrix material to change the electrical properties thereof is known in which the connection relative to the matrix material represents an n-dopant. In this, it is proposed to employ, as the dopant compound, a neutral metal complex rich in electrons and having a central atom as preferably a neutral or charged transition metal atom with a number of valence electrons of at least 16.

It has been known for many years, in particular in the case of organic polymeric semiconductor materials, that an effective electron transfer from a dopant (for example sodium) to the organic matrix (for example polyacetylene) is only possible if the difference between HOMO energy level (=ionisation potential) of the dopant and the LUMO energy level (=electron affinity) of the matrix is as small as possible.

Ultraviolet photoelectron spectroscopy (UPS) is the preferred method to determine the ionisation potential (e.g. R. Schlaf et al., J. Phys. Chem. B 103, 2984 (1999)). A related method, inverse photoelectron spectroscopy (IPES), is used to determine electron affinities (e.g. W. Gao et al., Appl. Phys. Lett. 82, 4815 (2003)), however, this is not as well-established. Alternatively, the solid state potentials can be estimated via electrochemical measurements of oxidation poten tials $E_{ox}$ or reduction potentials $E_{red}$, respectively, in the solution, e.g. by cyclic voltammetry (CV) (e.g. J. D. Anderson, J. Amer. Chem. Soc. 120, 9646 (1998)). Several papers state empirical formulae for converting the electrochemical voltage scale (oxidation potentials) to the physical (absolute) energy scale (ionisation potentials), e.g. B. W. Andrade et al., Org. Electron. 6, 11 (2005); T. B. Tang, J. Appl. Phys. 59, 5 (1986); V. D. Parker, J. Amer. Chem. Soc. 96, 5656 (1974); L. L. Miller, J. Org. Chem. 37, 916 (1972), Y. Fu et al., J. Amer. Chem. Soc. 127, 7227 (2005). No correlation of reduction potential and electron affinity is known as electron affinities can only be measured with difficulty. Hence, the electrochemical and physical energy scales are converted into each other in a simplified way by means of IP=4.8 eV+e*$E_{ox}$ (vs. ferrocene/ferrocenium) and EA-4.8 eV+e*$E_{red}$ (vs. ferrocene/ferrocenium), respectively, as described in B. W. Andrade, Org. Electron. 6, 11 (2005) (also see ref. 25-28 therein). The conversion of different standard potentials and redox pairs, respectively, is described in A. J. Bard, L. R. Faulkner, "Electrochemical Methods: Fundamentals and Applications", Wiley, 2$^{nd}$ Edition 2000, for example. Thus, it results from the depiction above that the exact determination of all energy values currently is not possible and that the presented values can only be construed as benchmarks.

The dopant functions in n-doping as an electron donor and transmits electrons to a matrix which is characterised by a sufficiently high electron affinity. That means that the matrix is reduced. By means of the transfer of electrons from the n-dopant to the matrix, the charge carrier density of the layer is increased. To which extent an n-dopant is able to release electrons towards a suitable matrix with electron affinity and thereby increase the charge carrier density and, as a consequence thereof, the electroconductivity depends in turn on the relative position of the HOMO of the n-dopant and the LUMO of the matrix in relation to one another. If the HOMO of the n-dopant is positioned above the LUMO of the matrix with electron affinity, an electron transfer can take place. If the HOMO of the n-dopant is arranged beneath the LUMO of the matrix with electron affinity, an electron transfer can likewise take place, provided that the energy difference between the two orbitals is sufficiently small to allow for a certain thermal population of the higher energy orbital. The smaller this energy difference, the higher the conductivity of the resulting layer should be. However, the highest conductivity can be anticipated in the case that the HOMO level of the n-dopant is higher than the LUMO level of the matrix with electron affinity. The conductivity can be measured conveniently and is a measure of how well the electron transmission from donor to acceptor functions, provided that the charge carrier mobilities of different matrices can be compared.

The conductivity of a thin-film sample is measured by the 2 point method. In this, contacts made from a conductive material, e.g. gold or indium tin oxide, are applied to a substrate. Thereafter, the thin film to be examined is applied to a large surface area of the substrate such that the contacts are covered by the thin film. After applying a voltage to the contacts, the current subsequently flowing is measured. Starting from the geometry of the contacts and the layer thickness of the sample, the conductivity of the thin-film material results from the resistance thus determined. The 2 point method is admissible when the resistance of the thin film is substantially higher than the resistance of the leads or the contact resistance. This is in the experiment ensured by a sufficiently large distance of the contacts and thus, the linearity of the voltage-current characteristic can be checked.

SUMMARY OF THE INVENTION

Investigations conducted by the inventors have shown that metal complex dopants of the structure I Structure I

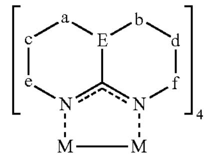

can be employed in an advantageous manner as dopants for an organic matrix material, as such a dopant solves the diffusion problem described above. For this reason, a dopant having the structure Ia

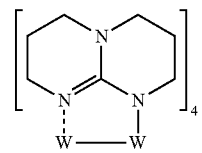

Structure Ia = $W_2(hpp)_4$ was tested as the dopant for conventional electron transport materials, such as $Alq_3$ (tris(8-hydroxyquinolinato)aluminium) or BPhen (4,7-diphenyl-1,10-phenanthroline).

DESCRIPTION OF THE EMBODIMENTS OF THE INVENTION

The ionisation potential in the gas phase of the dopant having the structure Ia is 3.6 eV. The corresponding ionisation potential of the solid can be estimated in accordance with Y. Fu et al. (J. Am. Chem. Soc. 2005, 127, 7227-7234) and is about 2.5 eV.

The results are given in the following Table 1.

TABLE 1

CV data, empirically determined LUMO energies and measured conductivities of different electron transport materials ($Balq_2$ = bis(2-methyl-8-quinolinato)-4-(phenylphenolato) aluminium(III), BPhen = bathophenanthroline, $Alq_3$: (tris(8-hydroxyquinoline) aluminium

| Matrix material | LUMO in eV (determined via CV with $Fc/Fc^+$ as internal standard) | σ (conductivity) in S/cm, non-doped | σ (conductivity) in S/cm, at a doping concentration of 5 mol % |
|---|---|---|---|
| $Alq_3$ | 2.4 | <1E−10 | 9.2E−8 |
| BPhen | 2.42 | <1E−10 | 4E−9 |
| $BAlq_2$ | 2.39 | <1E−10 | 8e−8 |

As can be seen from Table 1, the conductivities achieved with the known matrix materials are still insufficient and very low.

It is an object of the invention to provide improved matrix materials for doped organic semiconductor materials which overcome the disadvantages of the prior art. In particular, the conductivities should be improved when using the matrix materials. Furthermore, a semiconductor material should be made available which exhibits an increased charge carrier density and effective charge carrier mobility as well as an improved conductivity. The semiconductor material should show a high thermal stability which results, for example, from higher glass transition temperatures, higher sublimation temperatures and higher decomposition temperatures.

Finally, it is an object of the invention to provide a method for the production of the matrix materials.

The object of the invention is achieved by pyrido[3,2-h]quinazolines of the following structure 8:

Structure 8

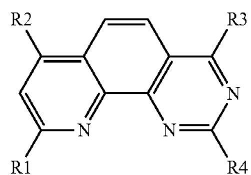

and/or 5,6-dihydro derivatives thereof wherein:

$R^1$ and $R^2$, substituted or unsubstituted, are aryl, heteroaryl, alkyl of the formula $CHR_2$ with R=alkyl with $C_1$-$C_{20}$, or alkyl of the formula $CR_3$ with R=alkyl with $C_1$-$C_{20}$;

$R^3$ is selected from H, substituted or unsubstituted, alkyl with $C_1$-$C_{20}$, aryl and heteroaryl;

$R^4$ is selected from H, substituted or unsubstituted, alkyl with $C_1$-$C_{20}$, aryl and heteroaryl, $NH_2$, NHR with R=alkyl with $C_1$-$C_{20}$, $NR_2$ with R=alkyl with $C_1$-$C_{20}$, N-alkylaryl, N-$aryl_2$, carbazolyl, dibenzazepinyl and CN.

$R^1$ and $R^2$, in the pyrido[3,2-h]quinazolines of the structure 8, should preferably not be II, CN, halogen, $NH_2$, NO, $NO_2$, OH, SH, OR, SR, COOR, CHO and alkyl of the formula $CH_3$ and $CH_2R$ with R=alkyl with $C_1$-$C_{20}$.

These pyrido[3,2-h]quinazolines and/or 5,6-dihydro derivatives thereof can be employed as matrix materials in doped organic semiconductor materials and then lead to improved conductivity results.

The pyrido[3,2-h]quinazolines and/or 5,6-dihydro derivatives can be produced in accordance with a method comprising the following steps:

reaction of a 2,4-disubstituted quinolinone of structure 4 with an aldehyde in the presence of a base to prepare a benzylidene hydroquinolinone 5 in accordance with the following reaction scheme:

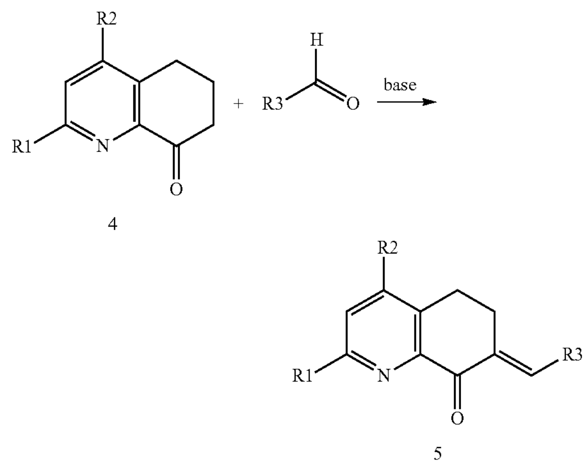

reaction of the benzylidene hydroquinolinone 5 with benzamidinium hydrochloride under basic conditions to prepare a 1,4,5,6-tetrahydropyrido[3,2-h]quinazoline 6 and subsequent oxidation to prepare a 5,6-dihydropyrido[3,2-h]quinazoline 7 in accordance with the following reaction scheme:

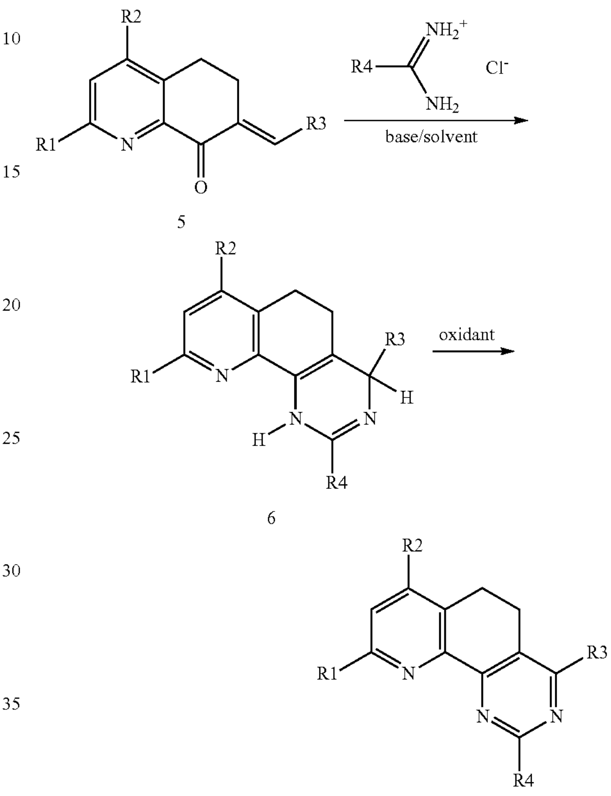

optionally aromatisation of the 5,6-dihydropyrido[3,2-h]quinazoline 7 to give the pyrido[3,2-h]quinazoline 8 in accordance with the following reaction scheme:

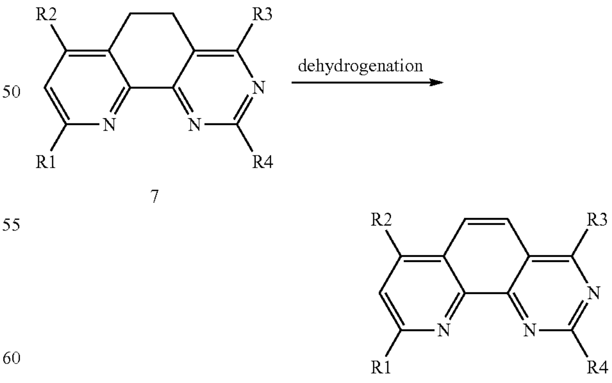

wherein $R^1$, $R^2$, $R^3$ and $R^4$ are defined as above in claim 1.

In this connection, it is preferred that potassium hydroxide and/or potassium tert-butoxide is used as the base.

Furthermore, it is preferably envisaged that chloranil is employed for the oxidation of the 1,4,5,6-tetrahydropyrido[3,2-h]quinazoline.

Likewise, it is preferably suggested that the aromatisation by Pd-catalysed dehydrogenation is taking place with Pd/C.

A doped organic semiconductor material is also according to the invention, comprising at least one organic matrix material which is doped with at least one dopant, wherein the matrix material is a pyrido[3,2-h]quinazoline and/or 5,6-dihydro derivative thereof.

In this connection, it is preferred that the matrix material can be reversibly reduced.

Alternatively, it is suggested that the matrix material is breaking down into stabile, redox inactive components during a reduction by means of the dopant, The dopant can be a metal complex.

The metal complex preferably has a structure I which is disclosed in patent application DE102004010954 (corresponds to WO05086251):

Structure I

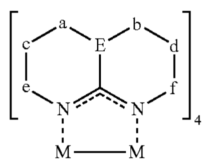

wherein M is a transition metal, preferably Mo or W; and wherein the structure elements a-f can have the meaning: a=—$CR_9R_{10}$—, b=—$CR_{11}R_{12}$—, c=—$CR_{13}R_{14}$—, d=—$CR_{15}R_{16}$—, e=—$CR_{17}R_{18}$— and f=—$CR_{19}R_{20}$—, wherein $R_9$-$R_{20}$ are independently hydrogen, alkyl with $C_1$-$C_{20}$, cycloalkyl with $C_1$-$C_{20}$, alkenyl with $C_1$-$C_{20}$, alkinyl with $C_1$-$C_{20}$, aryl, heteroaryl, —NRR or —OR, wherein R=alkyl with $C_1$-$C_{20}$, cycloalkyl with $C_1$-$C_{20}$, alkenyl with $C_1$-$C_{20}$, alkinyl with $C_1$-$C_{20}$, aryl or heteroaryl, wherein $R_9$, $R_{11}$, $R_{13}$, $R_{15}$, $R_{17}$, $R_{19}$ preferably=H and $R_{10}$, $R_{12}$, $R_{14}$, $R_{16}$, $R_{18}$, $R_{20}$ preferably=alkyl with $C_1$-$C_{20}$, cycloalkyl with $C_1$-$C_{20}$, alkenyl with $C_1$-$C_{20}$, alkinyl with $C_1$-$C_{20}$, aryl, heteroaryl, —NRR or —OR, or in the structure elements c and/or d, C can be replaced by Si, or optionally a or b or e or f is NR, with R=alkyl with $C_1$-$C_{20}$, cycloalkyl with $C_1$-$C_{20}$, alkenyl with $C_1$-$C_{20}$, alkinyl with $C_1$-$C_{20}$, aryl, heteroaryl, or optionally a and f or b and c are NR, with R=alkyl with $C_1$-$C_{20}$, cycloalkyl with $C_1$-$C_{20}$, alkenyl with $C_1$-$C_{20}$, alkinyl with $C_1$-$C_{20}$, aryl, heteroaryl, wherein the bonds a-c, b-d, c-e and d-f, but not a-c and e-e at the same time and not b-d and d-f at the same time, can be unsaturated, wherein the bonds a-c, b-d, c-e and d-f can be part of a saturated or unsaturated ring system which can also contain the heteroelements O, S, Se, N, P, Ge, Sn, or the bonds a-c, b-d, c-c and d-f are part of an aromatic or condensed aromatic ring system which can also contain the heteroelements O, S, Si, N, wherein the atom E is an element of the main group, preferably selected from the group of C, N, P, As, Sb, wherein the structure element a-c-b optionally is a constituent of a saturated or unsaturated ring system which can also contain the heteroelements O, S, Se, N, P, Si, Ge, Sn, or the structure element a-E-b optionally is a constituent of an aromatic ring system which can also contain the heteroelements O, S, Se, N.

It is particularly preferred that the dopant has the following structure Ia:

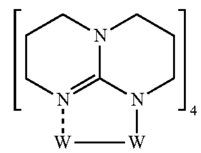

Structure Ia - $W_2(hpp)_4$

It is optionally also preferred that the dopant is an organic compound with a sufficiently high oxidation potential (HOMO).

It is optionally also preferred that the dopant is an alkaline and/or alkaline earth metal, preferably caesium.

It is also proposed that the organic semiconductor material according to the invention has an energy level for the lowest unoccupied molecule orbital (LUMO) which differs by 0 to 0.5 V from the ionisation potential (HOMO) of the dopant, preferably by 0 to 0.3 V, particularly preferably by 0 to 0.15 V.

One embodiment is characterised in that the matrix material has a LUMO energy level which is lower than the HOMO of the dopant. "Lower" means in this case that the LUMO energy level has a smaller numerical value than the HOMO energy level. As both variables are given as negative values starting from the vacuum level, this means that the absolute value of the HOMO energy value is smaller than the absolute value of the LUMO energy value.

It is also preferred that the concentration of the dopant is 0.5 to 25 percent by weight, preferably 1 to 15 percent by weight, particularly preferably 2.5 to 5 percent by weight.

An organic light-emitting diode is also according to the invention, comprising a semiconductor material according to the invention as well as benzylidene hydroquinolinones of the structure 5.

Surprisingly, it has been found that pyrido[3,2-h]quinazolines and/or 5,6-dihydro derivatives thereof can be employed as redox dopable matrix materials which can be doped with metal complex dopants, in particular those having the structure I.

When using such doped layers, the performance efficiency of an OLED according to the invention is increased.

The matrix materials employed according to the invention for the semiconductor material further exhibit an improved thermal stability in comparison with the prior art which is in particular attributable to higher glass transition temperatures and higher sublimation and decomposition temperatures.

It is preferred that the glass transition temperature Tg of the matrix material is higher than that of 4,7-diphenyl-1,10-phenanthroline (Tg=63° C.).

The matrix material preferably has an evaporation temperature of at least 200° C.

The matrix material preferably has a decomposition temperature of at least 300° C.

4,6,7-Triazaphenanthrenes, or systemic: pyrido[3,2-h]quinazolines, as described above, are hitherto not known from literature.

2,4-Disubstituted quinolinones of the structure 4 can be obtained in a three-step synthesis, starting from 2,4,6-triphenylpyrylium salts I and cyclohexanedione, via the step of the 8-oxo-1-benzopyrylium salts 3 (cf. Scheme 1). 8-Oxo-1-benzopyryliumperchlorate has already been described by Zimmermann et al. (T. Zimmermann, G. W. Fischer, 13. Olk, M. Findeisen: J. prakt. Chem. 331, 306-318 [1989]). As the larger-scale use of perchlorates is problematic in terms of security, the synthesis via the tetrafluoroborate 3 was newly developed in the present invention.

Scheme 1

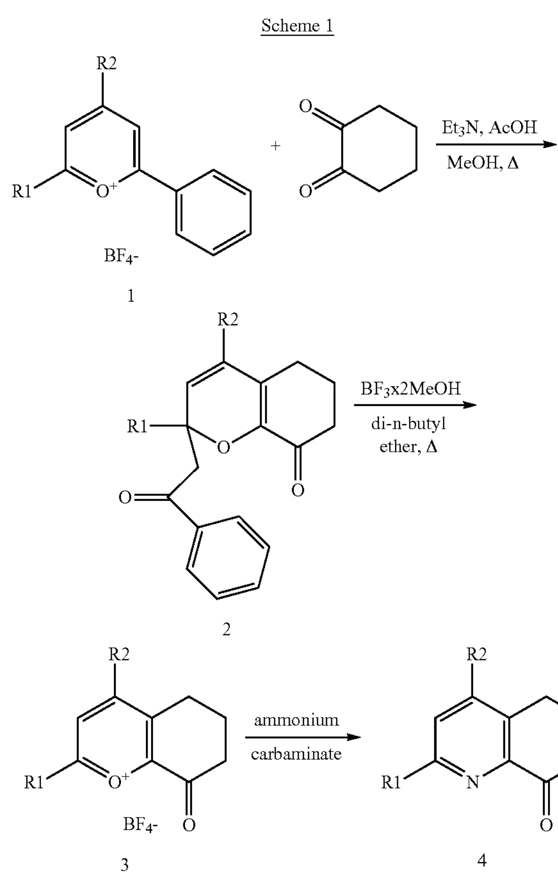

2,4-Disubstituted quinolinones of the structure 4 have been found as being particularly useful synthesis components for the construction of N-heterocycles. It is known that the condensation of quinolinones and aldehydes can be employed for the formation of benzylidene derivatives. Applying this reaction to the 2,4-disubstituted quinolinones in accordance with Scheme 2 leads to new benzylidene hydroquinolinones 5.

Scheme 2

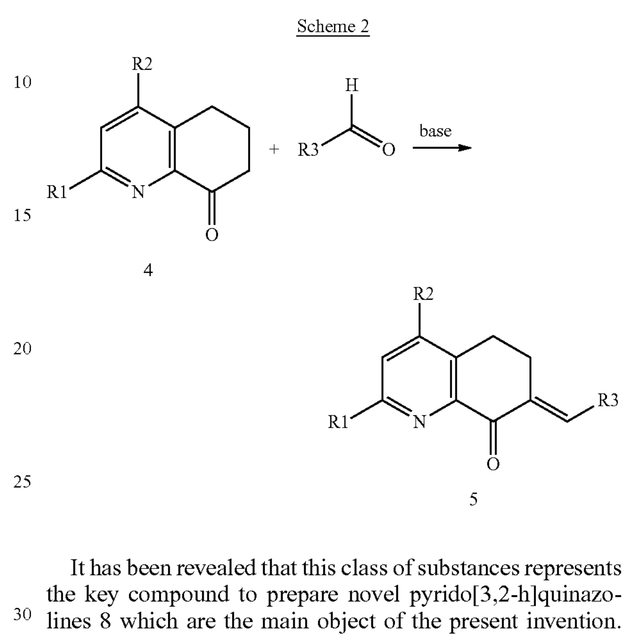

It has been revealed that this class of substances represents the key compound to prepare novel pyrido[3,2-h]quinazolines 8 which are the main object of the present invention. Surprisingly, it has been found that the reaction of the mentioned benzylidene hydroquinolinones 5 with benzamidinium hydrochloride under basic conditions leads to the formation of intermediates 6 which subsequently can be transferred by oxidation, for example with chloranil, to novel 5,6-dihydro[3,2-h]quinazolines 7 in accordance with Scheme 3.

Scheme 3

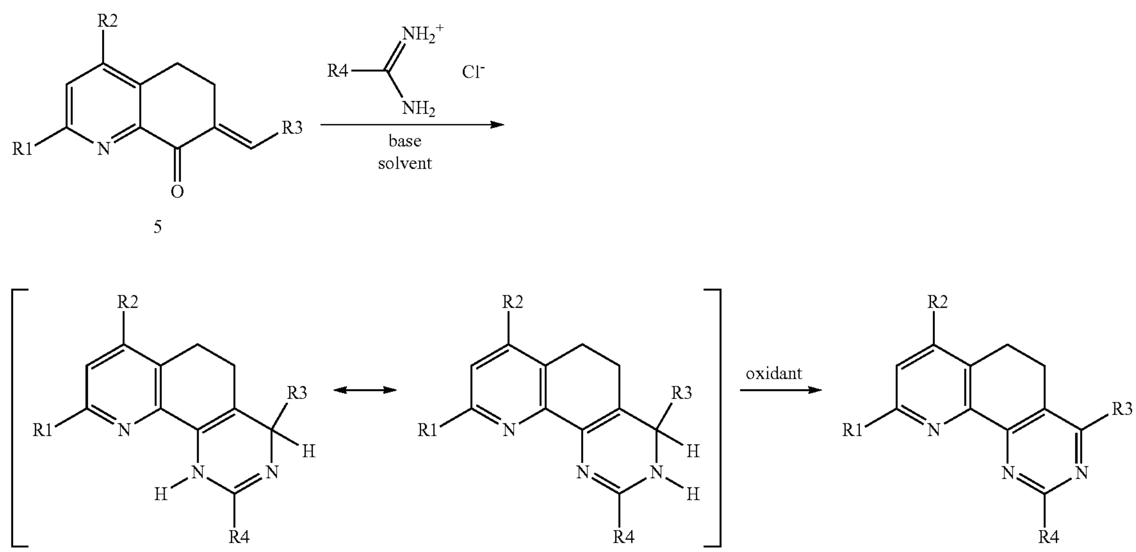

The subsequent aromatisation to novel pyrido[3,2-h] quinazolines 8 can take place, for example, by means of Pd-catalysed dehydrogenation of the dihydro compounds 7 in accordance with Scheme 4.

Scheme 4

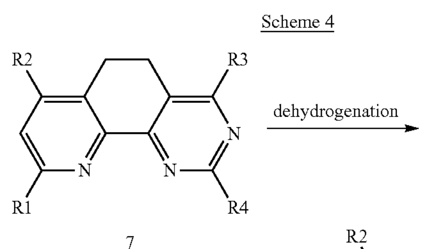

7

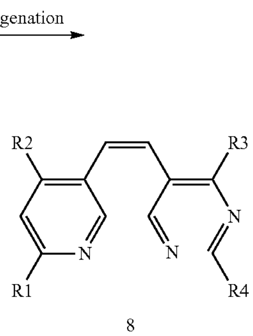

8

Other features and advantages of the invention become apparent from the following detailed description of preferred exemplary embodiments.

EXAMPLE 1

The following describes the complete synthesis of a derivative 8a of the new class of substances of the 2,4,7,9-tetrasubstituted pyrido[3,2-h]quinazolines 8.

Step 1: Synthesis of 5,6-dihydro-2-phenacyl-2,4-diphenyl-2H, 7H-1-benzopyran-8-one 2a

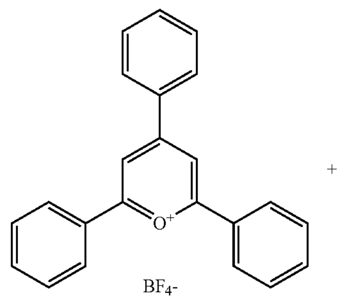

1a

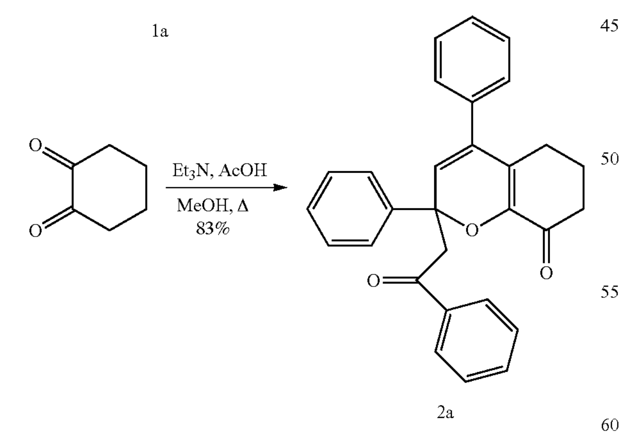

2a

Lit.: T. Zimmermann, G. W. Fisher, B. Olk, M. Findeisen: J. prakt. Chem. 331, 306-318 [1989]

A suspension of 13.51 g of 2,4,6-triphenylpyryliumtetrafluoroborate (34.1 mmol) and 4.78 g of cyclohexane-1,2-dione (42.6 mmol) is heated to boiling point in methanol, then a solution of 4.56 g of acetic acid (75.9 mmol) and 7.68 g of triethylamine (75.9 mmol) in a little methanol is added dropwise. After heating at reflux for 7 h, the solution is allowed to cool to room temperature. A light yellow precipitate is extracted by suction, washed in portions with 100 ml of ice-cold methanol and dried to constant weight. 11.37 g of a light yellow powder (79.3%) with a melting point of 178-179° C. (lit.: 182-184° C.) is obtained.

Step 2: Synthesis of 5,6,7,8-tetrahydro-8-oxo-2,4-diphenyl-1-benzopyryliumtetrafluoroborate 3a

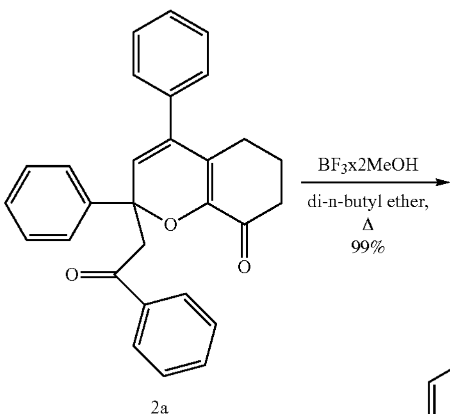

2a

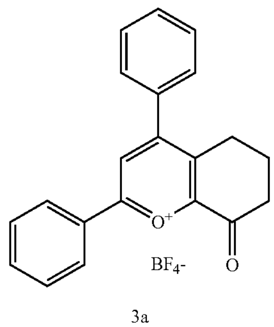

3a 25 ml of $BF_3$-dimethanol complex (50% of $BF_3$) is added to the suspension of 32.7 g of 5,6-dihydro-2-phenacyl-2,4-diphenyl-2H,7H-1-benzopyran-8-one (77.8 mmol) in 500 ml of di-n-butyl ether, during which the suspension changed colour to orange. Stirring of the suspension at room temperature is continued for 2 h and the suspension is subsequently heated to boiling point, thereafter boiled at reflux for 2 h. After cooling to room temperature, the precipitate is extracted by suction via a nutsche with paper filter, then washed with diethyl ether. After drying under high vacuum, 29.9 g (99%) of terracotta-coloured powder with a melting point of 213-214° C. (decomposition) is obtained. IR: The CO valence vibration band appears at 1718 $cm^{-1}$.

Step 3: Synthesis of 6,7-dihydro-2,4-diphenylquinolin-8(5H)-one 4a

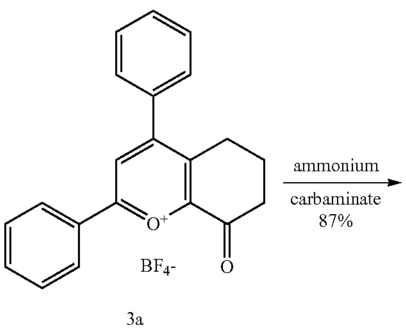

3a

-continued

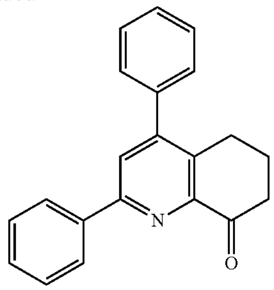

4a 12.44 g of 5,6,7,8-tetrahydro-8-oxo-2,4-diphenyl-1-benzopyryliumtetrafluoroborate (32 mmol) is suspended in 80 ml of distilled water and a solution of 25 g of ammonium carbaminate (320 mmol) in 200 ml of distilled water is added with stirring. After stirring at room temperature for 24 h, the solution is extracted by suction via a nutsche, washed with distilled water and dried by suction. The cream-coloured powder is washed in portions with diethyl ether and dried at 50° C. in a vacuum drying cabinet to constant weight: 8.39 g of ivory-coloured product (87.5%) with a melting point of 177-178° C. (decomposition). IR (ATR): The CO valence vibration band can be seen at 1700 $cm^{-1}$. $^1$H-NMR (500 MHz, $CDCl_3$): δ=8.09 (d, 2H, o-H of 2-phenyl), 7.79 (s, 1H, $H_3$), 7.56-733 (m, 8H, arom. H), 2.92 (t, 2H, J=5.75 Hz), 2.83 (t, 2H, J=6.56 Hz), 2.10 (p, 2H, J=5.75 Hz, J=6.56 Hz).

Step 4: Synthesis of 7-benzylidene-6,7-dihydro-2,4-diphenylquinolin-8(5H)-one 5a

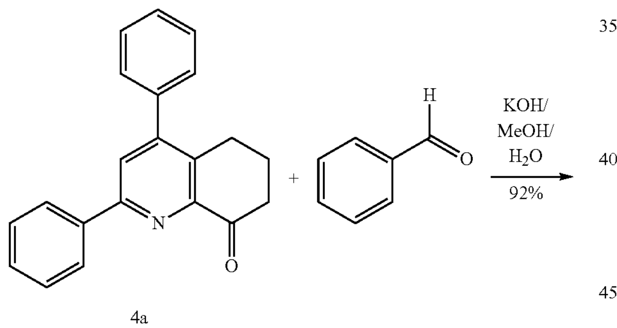

4a

5a

The solution of 5.6 g of potassium hydroxide (100 mmol) in 40 ml of distilled water is added to the suspension of 13.8 g of 6,7-dihydro-2,4-diphenylquinolin-8(5H)-one (46 mmol) with good stirring. The cream-coloured suspension is neutralised with 8 ml of glacial acetic acid and stirring at room temperature is continued for 30 min. The ivory-coloured product is extracted by suction, washed with 100 ml of distilled water, sharply dried by suction and air-dried. The ivory-coloured powder is suspended in 80 ml of methanol and stirring at room temperature is continued for 30 min. The precipitate is extracted by suction, washed with a little methanol and diethyl ether, dried by suction and dried at 60° C. in a vacuum drying cabinet to constant weight. 16.38 g of an ivory-coloured powder (91.9%) with a melting point of 185-187° C. (decomposition) is obtained. In an IR spectrum, the product shows the CO valence vibration band typical for chalcones at 1675 $cm^{-1}$. $^1$H-NMR (500 MHz, $CD_2Cl_2$): δ=8.13 (d, 2H, o-H of 2-phenyl), 7.93 (s, 1H, $H_9$), 7.87 (s, 1H, $H_3$), 7.56-7.32 (m, 13 arom. H), 3.09 (dt, 2H). 2.95 (t, 2H).

Step 5: Synthesis of 1,4,5,6-tetrahydro-2,4,7,9-tetraphenylpyrido[3,2-h]quinazoline 6a

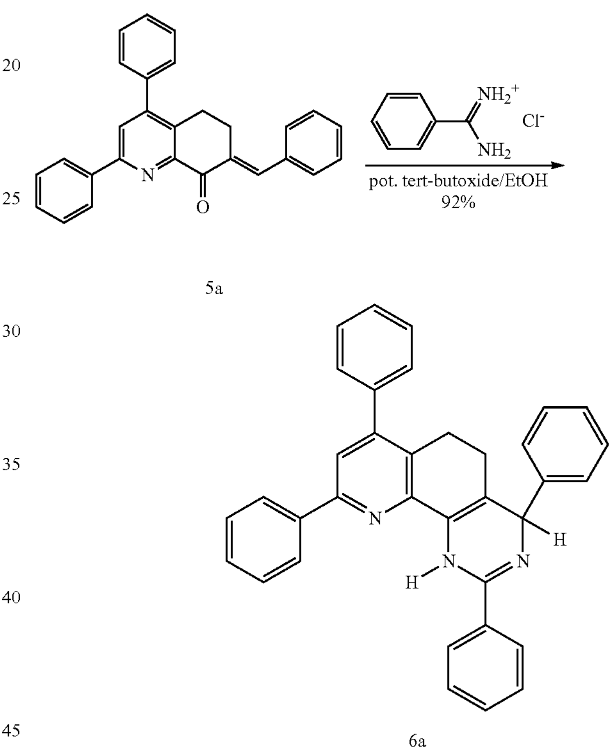

5a

6a 1.71 g of 7-benzylidene-6,7-dihydro-8-oxo-2,4-diphenylquinolin-8 (5H)-one (4.4 mmol) and 0.79 g of benzamidiniumchloride monohydrate (4 mmol) are suspended in 30 ml of ethanol and heated to boiling point. A solution of 0.56 g of potassium tert-butoxide (5 mmol) in 20 ml of ethanol is added dropwise to the suspension during which the precipitate gradually dissolves. After boiling at reflux for 1.5 h, a finely crystalline colourless precipitate forms. After heating at reflux for another 16 h, the suspension is cooled in air at room temperature. The ivory-coloured precipitate is extracted by suction, washed with distilled water and rewashed with 30 ml of ethanol. After drying under high vacuum, 2 g (92.8%) of almost white, cotton-like powder with a melting point of 142-144° C. (no clear melt) is obtained. The TGA results in a melting point of 139° C., the DSC a $T_g$ of 74° C. In an IR spectrum, the product shows a broadened NH band at 3385 $cm^{-1}$ as well as in low intensity a band at 1687 $cm^{-1}$ which can be assigned to an isolated C═N band. The slightly more intensive band at 1630 $cm^{-1}$ is attributable to the dihydroquinoline ring. $^1$H-NMR (500

MHz, $CD_2Cl_2$): δ=8.46 (s, br, NH), 8.12-8.04 (m, 2H, o-H of 9-phenyl), 7.95-7.88 (m, 2H, o-H of 9-phenyl), 7.60 (s, 1H, $H_8$), 7.56-7.22 (m, 16H, arom. H), 5.40 (s, 1H, $H_4$), 2.99-2.80 (m, 2H), 2.30-2.18 (m, 1H), 2.18-2.06 (m, 1H).

Step 6: Synthesis of 5,6-dihydro-2,4,7,9-tetraphenylpyrido[3,2-h]quinazoline 7a

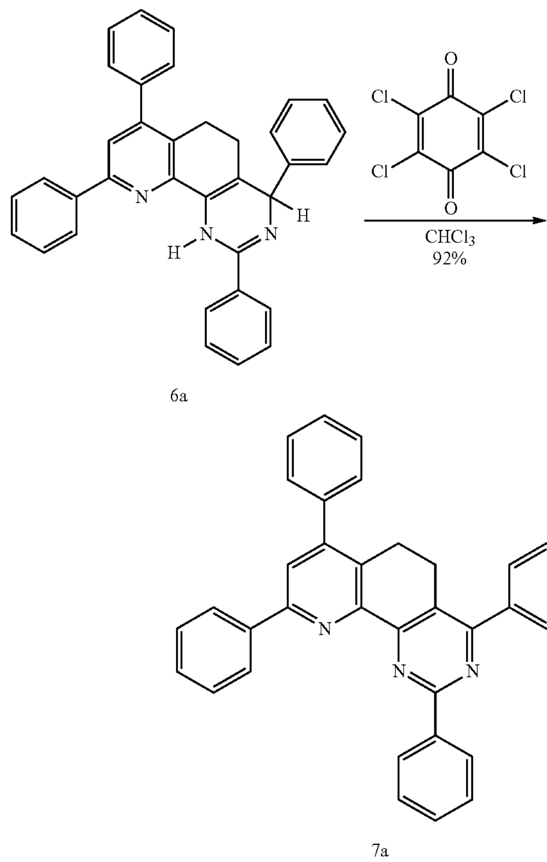

3.43 g of 2,4,7,9-tetraphenyl-1,4,5,6-tetrahydropyrido[3,2-h]quinazoline (7 mmol) is dissolved in 50 ml of chloroform; then 1.97 g of chloranil (8 mmol) is added in one portion. Stirring of the resulting brownish suspension at room temperature is continued. After only 30 min, the DC examination of the supernatant solution (aluminium oxide; eluent: methylene dichloride) shows that the spot of the starting material has widely disappeared. Stirring of the suspension at room temperature is continued for another 2 h and it is extracted by suction and air-dried. The cream-coloured polder (1.35 g) is washed with 50 ml of chloroform in portions. 100 ml of 6% potassium carbonate solution is added to the chloroform solution and it is vigorously stirred. The aqueous phase is separated in a separatory funnel, shaken twice with 25 ml of chloroform each time and discarded. The combined chloroform phases are washed with distilled water and dried after separating the aqueous phase over anhydrous potassium carbonate. The dried, light yellow chloroform solution is filtered with a pleated filter and 50 ml of cyclohexane is added. The chloroform is widely removed by distillation on a rotavapor under reduced pressure. The obtained cream-coloured microcrystalline powder is extracted by suction, washed with cyclohexane and dried under high vacuum:

3.10 g of ivory-coloured microcrystalline product (91%) with a melting point of 298-299° C. is obtained. The TGA shows the melting peak of 299° C. After cooling the sample, the $2^{nd}$ heating process shows a $T_g$ of 103° C. In an IR spectrum, the NH band at 3385 $cm^{-1}$ and the C═N bands at 1687 $cm^{-1}$ and 1630 $cm^{-1}$ of the starting material have disappeared, instead a new, split band can be observed in low intensity at 1591 $cm^{-1}$ or 1581 $cm^{-1}$, respectively. $^1$H-NMR (500 MHz, $CDCl_3$): δ=8.78 (d, 2H, o-H of 2-phenyl), 8.31 (d, 2H, o-H of 9-phenyl), 7.83 (s, 1H, $H_8$), 7.78-7.73 (m, 2H, o-H of 4-phenyl), 7.64-7.36 (m, 14H, arom. H), 3.08 (dd, 2H), 2.95 (dd, 2H).

5,6-Dihydro-2,4,7,9-tetraphenylpyrido[3,2-h]quinazoline 7a possesses in THF the reduction half-wave potential $E_{1/2}^{Ered}$=−2.27 V ($\Delta E_T^{Ered}$=70 mV) vs. Fc/Fc$^+$. The reduction is reversible. It is not possible to measure an oxidation potential within the window available in THF.

Step 7: Synthesis of 2,4,7,9-tetraphenylpyrido[3,2-h]quinazoline 8a

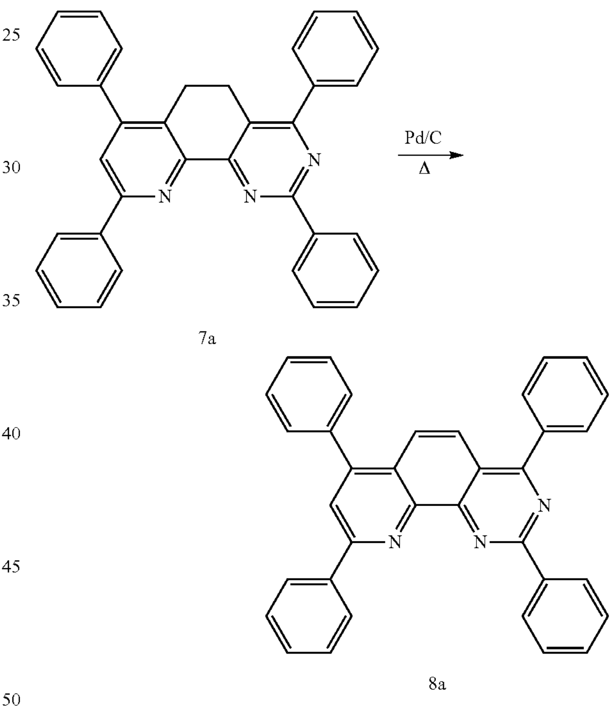

940 mg of 5,6-dihydro-2,4,7,9-tetraphenylpyrido[3,2-h]quinazoline (1.93 mmol) is suspended in 50 ml of diethylene glycol and brought into solution by heating, then 200 mg of Pd/C (5%) is added in portions. The suspension is heated to boiling point, heated at reflux for 10 h and subsequently cooled in air at room temperature. After an DC examination, 50 ml of distilled water is added. Stirring of the suspension at room temperature is continued for 30 min, it is filtered and the filter cake is washed with distilled water in portions and sharply dried by suction. The black residue which is interspersed with white crystals is washed on a sintered-glass filter with 400 ml of chloroform in portions. The brownish-yellow filtrate is dried over anhydrous sodium sulphate, filtered and evaporated to dryness. The cream-coloured residue is dissolved in 50 ml of chloroform with slight heating and filtered in 100 ml of cyclohexane. The light yellow solution is concentrated to half of its volume, during which an ivory-coloured, cotton-like precipitate is deposited. This is extracted by suction, washed with a little cyclohexane and diethyl ether and dried under high vacuum: 0.82 g (87.5%) of a microcrystalline white powder with a very exact melting point of 327° C. is obtained. At first, a glass transition temperature $T_g$ cannot be measured. The cooling curve which is recorded in a controlled fashion (10 K/min) after the 2nd heating process shows recristallisation at 272° C. After fast cooling, a $T_g$ of 103° C. is measured in the DSC. The $^1$H-NMR spectrum only includes the signals of 5,6-dihydro-2,4,7,9-tetraphenylpyrido[3,2-h]quinazoline. The signals of the methylene protons of the starting material at 3.07 (dd, 2H) and 2.95 (dd, 2H) have disappeared.

Tetraphenylpyrido[3,2-h]quinazoline 8a possesses in MeCN the reduction half-wave potential $E_{1/2}^{Ered}$=−2.06 V ($\Delta E_T^{Ered}$=70 mV) vs. Fc/Fc$^+$. The reduction is reversible. It is not possible to measure an oxidation potential within the window available in MeCN.

Up to 500° C., it was not possible to determine a decomposition temperature of 8a (DSC) under nitrogen. Therefore, the class of compounds can be put under a very high thermal stress. The sublimination temperature of 8a is 259° C. and thus is markedly higher than the bench mark of 200° C.

The result of a comparison of the glass transition temperatures of 7a and 8a with BPhen is that the morphologic stability of BPhen is very low, that of 7a and 8a, in contrast, is markedly increased.

EXAMPLE 2

The following describes the partial synthesis of a derivative 8b, starting from 4a.

Step 4: Synthesis of 7-toluidene-6,7-dihydro-2,4-diphenylquinolin-8(5H)-one 5b A solution of 1.5 g of potassium hydroxide (36.7 mmol) in 15 ml of distilled water is added to the suspension of 5 g of 6,7-dihydro-2,4-diphenylquinolin-8(5H)-one (16.7 mmol). The resulting suspension is stirred in a sealed round-bottomed flask at room temperature for 1 d, neutralised with glacial acetic acid and stirring at room temperature is continued for 30 min. The precipitate is extracted by suction, washed with distilled water and dried. The ivory-coloured powder is suspended in 80 ml of methanol and stirring at room temperature is continued for 30 min. The precipitate is extracted by suction, washed with methanol and diethyl ether and dried under high vacuum: 3.2 g of ivory-coloured powder (47%) with a melting point of 175-185° C. (decomposition). The product shows the CO valence vibration band typical for chalcones at 1675 cm$^{-1}$.

$^1$H-NMR (500 MHz, $CD_2Cl_2$): δ=8.13 (d, 2H, o-H of 2-phenyl), 7.96 (s, 1H, $H_9$), 7.81 (s, 1H, $H_3$), 7.56-7.32 (m, 11 arom. H), 7.21 (d, 2H of phenyl), 3.08 (t, 2H), 2.94 (t, 2H), 2.37 (8s, 3H).

Step 5: Synthesis of 1,4,5,6-tetrahydro-2,7,9-triphenyl-4-p-toluylpyrido[3,2-h]quinazoline 6b 3 g of 7-toluidene-6,7-dihydro-2,4-diphenylquinolin-8(5H)-one (7.5 mmol) and 1.6 g of benzamidiniumchloride monohydrate (8.2 mmol) are suspended in 50 ml of ethanol and heated to boiling point. A solution of 1.2 g of potassium tert-butoxide (10 mmol) in 20 ml of ethanol is added dropwise to the suspension during which the precipitate gradually dissolves. After boiling at reflux for 24 h, the suspension is cooled at room temperature. The precipitate is extracted by suction, washed with distilled water and ethanol and dried under high vacuum to constant weight. 2.6 g of product (57%) with a melting point of 128-133° C. is obtained.

In an IR spectrum (ATR), the product shows a broadened NH band at 3418 cm$^{-1}$ as well as in low intensity a band at 1625 cm$^{-1}$ which can be assigned to an isolated C═N band.

$^1$H-NMR (500 MHz, $CD_2Cl_2$): δ=8.43 (s, br, NH), 8.09 (d, 2H, o-H of 9-phenyl), 7.93-7.91 (m, 2H, o-H of 2-phenyl), 7.59 (s, 1H, $H_8$), 7.54-7.43 (m, 10H, arom. H), 7.38 (d, 2H), 7.35 (d, 2H), 7.15 (d, 2H), 5.35 (s, 1H, $H_4$), 2.95-2.82 (m, 2H), 2.32 (s, 3H), 2.26-2.20 (m, 1H), 2.15-2.08 (m, 1H).

Step 6b: Synthesis of 5,6-dihydro-2,7,9-triphenyl-4-p-toluylpyrido[3,2-h]quinazoline 7b 2.5 g of 2,4,7,9-tetraphenyl-1,4,5,6-tetrahydropyrido[3,2-h]quinazoline (4.96 mmol) is dissolved in 70 ml of chloroform; then 1.46 g of chloranil (5.95 mmol) is added in one portion. Stirring of the resulting brownish suspension at room temperature is continued. After only 30 min, the DC examination of the supernatant solution (aluminium oxide; eluent: methylene dichloride) shows that the reaction is complete. The suspension is filtered with a D4 sintered-glass filter. 100 ml of 6% potassium carbonate solution is added to the chloroform solution and it is vigorously stirred. The aqueous phase is shaken twice with 25 ml of chloroform each time and then discarded. The combined chloroform phases are washed with distilled water, dried over anhydrous potassium carbonate, filtered and 50 ml of cyclohexane is added. The chloroform is widely removed by distillation under reduced pressure. The obtained powder is extracted by suction, washed with a little cyclohexane and dried under high vacuum: 2.1 g (85%) of ivory-coloured microcrystalline product with a melting point of 261° C. and a $T_g$ of 109° C. is obtained. $^1$H-NMR (500 MHz, $CDCl_3$): δ=8.77 (d, 2H, o-H of 2-phenyl), 8.29 (d, 2H, o-H of 9-phenyl), 7.81 (s, 1H, $H_8$), 7.67 (d, 2H, o-H of 4-phenyl), 7.56-7.44 (m, 10H, arom. H), 7.42 (d, 2H, phenyl), 7.32 (d, 2H, phenyl) 3.07 (m, 2H), 2.93 (m, 2H), 2.44 (s, 3H).

5,6-Dihydro-2,7,9-triphenyl-4-p-toluylpyrido[3,2-h]quinazoline 7b possesses in THF the reduction half-wave potential $E_{1/2}^{Ered}$=−2.29 V ($\Delta E_T^{Ered}$=70 mV) vs. Fe/Fc$^+$. The reduction is reversible. It is not possible to measure an oxidation potential within the window available in THF.

Step 7: Synthesis of 2,7,9-triphenyl-4-p-toluylpyrido[3,2-h]quinazoline 8b 2 g of 5,6-dihydro-2,7,9-triphenyl-4-p-toluylpyrido[3,2-h]quinazoline (3.98 mmol) is suspended in 100 ml of diethylene glycol and brought into solution by heating, then 500 mg of Pd/C (10%) is added in portions. The suspension is heated to boiling point and boiled at reflux until the starting material can no longer be detected, as determined by DC examination. 50 ml of distilled water is added, stirring at room temperature is continued for 30 min and it is filtered. The residue is washed with 300 ml of distilled water in portions and dried by suction. The residue is then washed with 600 ml of chloroform in portions. The filtrate is dried over anhydrous sodium sulphate and filtered. The solution is evaporated to dryness under reduced pressure. The cream-coloured residue is dissolved in 50 ml of chloroform with slight heating and filtered in 100 ml of cyclohexane. The light yellow solution is concentrated to half of its volume under reduced pressure, during which an ivory-coloured, cotton-like precipitate is deposited. The precipitate is extracted by suction, washed with cyclohexane and diethyl ether and dried under high vacuum. 1.5 g (75%) of a microcrystalline white, cotton-like powder with a melting temperature of 261° C. is obtained, A $T_g$ could not be detected by means of DSC.

The $^1$H-NMR spectrum in $CDCl_3$ only includes the signals of 5,6-dihydro-2,4,7,9-tetraphenylpyrido[3,2-h]quinazoline. The signals of the methylene protons of the starting material at 3.07 (dd, 2H) and 2.95 (dd, 2H) have disappeared, i.e., the dehydrogenation has been completed.

2,7,9-Triphenyl-4-p-toluylpyrido[3,2-h]quinazoline 8b possesses in THF the reduction half-wave potential $E_{1/2}^{Ered}=-2.29$ V ($\Delta E_T^{Ered}=70$ mV) vs. Fe/Fe$^+$. The reduction is reversible. It is not possible to measure an oxidation potential within the window available in THF.

Up to 500° C., it was not possible to determine a decomposition temperature of 8b (DSC) under nitrogen. Therefore, the class of compounds can be put under a very high thermal stress. The sublimination temperature of 8b is 272° C. and thus is markedly higher than the bench mark of 200° C.

The result of a comparison of the glass transition temperatures of 7b and 8b with BPhen is that the morphologic stability of BPhen is very low, that of 7b and 8b), in contrast, is markedly increased.

EXAMPLE 3

A glass substrate is provided with contacts made from indium tin oxide. Subsequently, a layer of 7a doped with a dopant of the structure Ia is formed on the substrate. The doping concentration of the dopant Ia is 5 mol %. The conductivity of the layer at room temperature is $4.13*10^{-5}$ S/cm.

EXAMPLE 4

A glass substrate is provided with contacts made from indium tin oxide. Subsequently, a layer of 8a doped with a dopant of the structure Ia is formed on the substrate. The doping concentration of the dopant Ia is 5 mol %. The conductivity of the layer at room temperature is $1.84*10^{-5}$ S/cm.

EXAMPLE 5

A glass substrate is provided with contacts made from indium tin oxide. Subsequently, a layer of 7b doped with a dopant of the structure Ia is formed on the substrate. The doping concentration of the dopant Ia is 5 mol %. The conductivity of the layer at room temperature is $2.05*10^{-5}$ S/cm.

EXAMPLE 6

A glass substrate is provided with contacts made from indium tin oxide. Subsequently, a layer of 8b doped with a dopant of the structure Ia is formed on the substrate. The doping concentration of the dopant Ia is 5 mol %. The conductivity of the layer at room temperature is $2.76*10^{-5}$ S/cm.

COMPARATIVE EXAMPLE 7

A Comparative Example 7 was performed analogous to the procedure of Examples 3 to 6, but the BPhen known from literature was used instead of the matrix material 7a, 8a and 7b, 8b, respectively. The obtained conductivity of the layer is $4*10^{-9}$ S/cm.

A comparison of the conductivities from Examples 3 to 6 with the conductivities for the matrix materials $Alq_3$, BPhen or $BAlq_2$ known from the prior art (Table 1 and Comparative Example 7) thus shows for the class of substances 8 according to the invention a by 3-4 orders of magnitude markedly improved conductivity.

EXAMPLE 8

A substrate made from glass is provided with indium tin oxide contacts. Thereupon, the layers: Spiro TTB doped with the p-dopant 2-(6-dicyanomethylene-1,3,4,5,7,8-hexafluoro-6H-naphthalen-2-ylidene)malononitrile (50 nm, 1.5 wt %)/N,N'-di(naphthalen-2-yl)-N,N'-diphenylbenzidine (10 nm), N,N'-di(naphthalen-2-yl)-N,N'-diphenylbenzidine doped with the emitter iridium(III) bis(2-methyldibenzo[f,h] quinoxaline) (acetylacetonate) (20 nm, 10 wt %)/2,4,7,9-tetraphenylphenanthroline (10 nm)/8a doped with Ia (60 nm, 8 wt %)/Al (100 nm) are then deposited successively. The organic light-emitting diode thus produced emits orange red light and has the following operational parameters at 1000 cd/m$^2$: 3.2 V and 20 cd/A.

COMPARATIVE EXAMPLE 9

(Prior Art)

An OLED structure as in Example 6 was produced. In this, the undoped electron transport layer 8a is used instead of the electron transport layer 8a n-doped with Ia. This OLED has the following operational parameters at 100 cd/m$^2$: 18.2 V and 7.4 cd/A.

Using 8a doped with Ia as the electron transport layer also results in that an OLED structure has a lower operating voltage and/or a higher current efficiency. Consequently, the performance efficiency of the component is also increased.

The features disclosed in the description and in the claims can be essential to implement the invention in its different embodiments both alone and in any combination.

The invention claimed is:

1. A benzylidene hydroquinolinone of the formula 5,

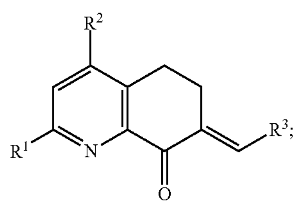

wherein:

$R^1$ and $R^2$ are selected independently from a, substituted or unsubstituted, aryl, heteroaryl, alkyl of the formula $CHR_2$, or alkyl of the formula $CR_3$, wherein each R is selected independently from a $C_1$-$C_{20}$ alkyl; and $R^3$ is selected from H, or a, substituted or unsubstituted, $C_1$-$C_{20}$alkyl, aryl, or heteroaryl.

2. A method for preparing a benzylidene hydroquinolinone of the formula 5 according to claim 1, wherein a 2,4-disubstituted quinolinone of structure 4 is reacted with an aldehyde in the presence of a base:

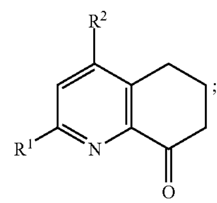

wherein:

$R^1$ and $R^2$ are selected independently from a, substituted or unsubstituted, aryl, heteroaryl, alkyl of the formula $CHR^2$, or alkyl of the formula $CR_3$, wherein each R is selected independently from a $C_1$-$C_{20}$ alkyl.

* * * * *

UNITED STATES PATENT AND TRADEMARK OFFICE

CERTIFICATE OF CORRECTION

| | | |
|---|---|---|
| PATENT NO. | : 8,115,003 B2 | Page 1 of 1 |
| APPLICATION NO. | : 12/868465 | |
| DATED | : February 14, 2012 | |
| INVENTOR(S) | : Josef Salbeck, Manfred Kussler and Andrea Lux | |

It is certified that error appears in the above-identified patent and that said Letters Patent is hereby corrected as shown below:

At column 20, line 63, delete "$CHR^{2}$" and insert -- $CHR_2$ --.

Signed and Sealed this
Tenth Day of April, 2012

David J. Kappos
*Director of the United States Patent and Trademark Office*